US005667767A

United States Patent [19]

Greff et al.

[11] Patent Number: 5,667,767

[45] Date of Patent: Sep. 16, 1997

[54] COMPOSITIONS FOR USE IN EMBOLIZING BLOOD VESSELS

[75] Inventors: Richard J. Greff, Yorba Linda; Michael L. Jones, Capistrano Beach; Scott Evans, Santa Ana, all of Calif.

[73] Assignee: Micro Therapeutics, Inc., San Clemente, Calif.

[21] Appl. No.: 507,863

[22] Filed: Jul. 27, 1995

[51] Int. Cl.$^6$ .................. C08J 3/00; C08K 5/41; C08L 29/04; A61K 31/765

[52] U.S. Cl. .............. 424/9.411; 424/9.4; 424/9.41; 424/78.37; 523/113; 523/105; 523/136; 524/155; 524/173; 524/408; 524/430; 524/439; 524/423; 524/436; 604/20; 604/52; 604/53; 604/56; 604/70

[58] Field of Search .................. 424/677, 709, 424/9.4, 9.41, 9.411, 78.37; 523/136, 113, 105; 524/155, 173, 408, 430, 439, 423, 436; 604/20, 52, 53, 56, 70, 21

[56] References Cited

U.S. PATENT DOCUMENTS

| 4,079,124 | 3/1978 | Winchell | 424/4 |
| 4,631,188 | 12/1986 | Stoy et al. | 424/81 |
| 4,795,741 | 1/1989 | Leshchiner et al. | 514/21 |
| 4,938,763 | 7/1990 | Dunn et al. | 604/891.1 |
| 5,202,352 | 4/1993 | Okada et al. | 514/475 |
| 5,443,454 | 8/1995 | Tanabe et al. | 604/264 |
| B1 4,938,763 | 7/1995 | Dunn et al. | 604/891.1 |

FOREIGN PATENT DOCUMENTS

| 5-57014 | 3/1993 | Japan . |
| 5-253283 | 10/1993 | Japan . |
| 6-107549 | 4/1994 | Japan . |

OTHER PUBLICATIONS

Toxicology, Amdur et al., Editors, *Toxic Effects of Metals*, 4th Edition, pp. 661–664, Pergamon Press, New York, New York.

Guglielmi, et al., *Electrothrombosis of Saccular Aneurysms via Endovascular Approach*, J. Neurosurg., 75:8–14 (1991).

Kinugasa, et al., *Early Treatment of Subarachnoid Hemorrhage After Preventing Rerupture of an Aneurysm*, J. Neurosurg., 83:34–41 (1995).

Kinugasa, et al., *Prophylatic Thrombosis to Prevent New Bleeding and to Delay Aneurysm Surgery*, Neurosurgery, 36(4):661–667 (1995).

Kinugasa, et al., *Direct Thrombosis of a Pseudoaneurysm after Obliteration of a Carotid–Cavernous Fistula with Cellulose Acetate Polymer: Technical Case Report*, Neurosurgery, 35(4):755–760 (1994).

Kinugasa, et al., *Direct Thrombosis of Aneurysms with Cellulose Acetate Polymer, Part II: Preliminary Clinical Experience*, J. Neurosurg., 77:501–507 (1992).

Mandai, et al., *Direct Thrombosis of Aneurysms with Cellulose Acetate Polymer, Part I: Results on Thrombosis in Experimental Aneurysms*, J. Neurosurg., 77:497–500 (1992).

Miyatake, et al., *Cobb's Syndrome and its Treatment with Embolization*, J. Neurosurg., 72:497–499 (1990).

Sadato, et al., *Experimental Study and Clinical Use of Poly(vinyl acetate) Emulsion as Liquid Embolisation Material*, Neuroradiology, 36:634–641 (1994).

Sugiu, et al., *Direct Thrombosis of Experimental Aneurysms with Cellulose Acetate Polymer (CAP): Technical Aspects, Angiographic Follow Up, and Histological Study*, J. Neurosurg., 83:531–538 (1995).

Taki, et al., *A New Liquid Material for Embolization of Arteriovenous Malformatoins*, Am. J. Neuroradiology, 11:163–168 (1990).

Taki, et al., *Selection and Combination of Various Endovascular Techniques in the Treatment of Giant Aneurysms*, J. Neurosurg., 77:37–42 (1992).

Terada, et al., *Embolization of Arteriovenous Malformations with Peripheral Aneurysms using Ethylene Vinyl Alcohol Copolymer*, J. Neurosurg., 75:655–660 (1991).

Yamashita, et al, *Characteristics of Ethylene Vinyl Alcohol Copolymer (EVAL) Mixtures*, Am. J. Neuroradiology, 15:1103–1105 (1994).

Medical Tribune, "Possibility and Limit of Intravascular Surgery", Taki, Oct. 26, 1989, pp. 46–47.

*Primary Examiner*—Patrick Niland
*Attorney, Agent, or Firm*—Burns, Doane, Swecker & Mathis, L.L.P.

[57] ABSTRACT

Disclosed are compositions suitable for use in embolizing blood vessels which compositions comprise an ethylene vinyl alcohol copolymer, a biocompatible solvent and a water insoluble contrasting agent selected from the group consisting of tantalum, tantalum oxide and barium sulfate. Also disclosed are methods for embolizing a blood vessel using the compositions described herein.

15 Claims, No Drawings

COMPOSITIONS FOR USE IN EMBOLIZING BLOOD VESSELS

BACKGROUND OF THE INVENTION

Field of the Invention

This invention is directed to compositions suitable for use in embolizing blood vessels. In particular, this invention is directed to embolizing compositions comprising an ethylene vinyl alcohol copolymer, a biocompatible solvent and a water insoluble contrasting agent. The compositions of this invention find particular utility in embolizing blood vessels in, for example, the treatment of aneurysms and in ablating diseased tissues.

References

The following publications are cited in this application as superscript numbers: [1]Casarett and Doull's *Toxicology*, Amdur et al., Editors, Pergamon Press, New York, pp. 661–664 (1975) [2]Taki, et al., "A New Liquid Material for Embolization of Arteriovenous Malformations", *American Society of Neuroradiology*, 11: 163–168 (1990) [3]Terada, et al., "Embolization of Arteriovenous Malformations with Peripheral Aneurysms Using Ethylene Vinyl Alcohol Copolymer", *J. Neurosurg.*, 75: 655–660 (1991)

All of the above references are herein incorporated by reference in their entirety to the same extent as if each individual reference was specifically and individually indicated to be incorporated herein by reference in its entirety.

State of the Art

It is desirable in many clinical situations to embolize blood vessels to prevent/control bleeding (e.g., organ bleeding, gastrointestinal bleeding, vascular bleeding, bleeding associated with an aneurysm) or to ablate diseased tissue (e.g., tumors, etc.). Embolization of blood vessels has heretofore employed polymer compositions and particulates, e.g., silicone, metallic coils, sclerosing materials and the like. Polymeric materials employed in the polymeric compositions include those which polymerize in situ at the vascular site (e.g., cyanoacrylates) and those wherein a preformed polymer in situ precipitates from a carrier solution at the vascular site.

The in situ polymerization of cyanoacrylates delivered via a catheter causes complications due to premature polymerization and/or adhesion of the polymer to the catheter. Accordingly, there has been recent focus on incorporating preformed polymeric materials into embolization compositions. Ideally, such compositions should be easy to deliver (e.g., low viscosity) and should cause rapid embolization in the intended vascular site. Additionally, these compositions should be sterile, stable, biocompatible and radiopaque. This last property is necessary in order to monitor injection of the embolizing composition into the vascular site and to confirm its presence after the procedure is complete.

Current embolizing compositions employing preformed polymers typically fail to meet one or more of the requirements of ideal embolizing compositions and a compromise must be made in selecting the embolizing agents relative to the given clinical case. At times, embolization of the blood vessel, although called for by the clinical condition of the subject, is not performed due to difficulties in selecting an embolizing composition suitable for use in the given case.

Failure of such embolizing compositions to meet these ideal requirements often arises from the particular combination of embolizing and contrast agents used in the embolizing composition. Specifically, the biocompatible embolizing agent should produce a well defined coherent plug/solid upon contact with blood and the contrast agent should be encapsulated in the formed solid in order to permit adequate definition of the location of embolism formation. While certain compositions comprising an embolizing agent, a contrast agent and a biocompatible solvent such as dimethylsulfoxide (DMSO) have heretofore been disclosed, the choice of embolizing agent in combination with contrast agent is critical to successful use in embolizing conditions. For example, the selected embolizing agent must be biocompatible, capable of rapid precipitation to form a solid, space-filling material and compatible with the selected contrast agent. Additionally, the resulting solid material must be sufficiently coherent so as to minimize fragmentation which results in smaller solid materials being incorporated within the circulation system. As is apparent, the presence of solid materials in the circulation system can lead to embolization of blood vessels at undesired locations. In the extreme, unintended embolization of essential blood vessels can lead to subject death.

The choice of contrast agent relative to the embolizing agent is particularly critical and contrast agents heretofore employed for gastrointestinal tract applications and intravascular injections are not always suitable for use in embolizing blood vessels. For example, while bismuth trioxide is a well known contrast agent, recent evidence indicates that exposure to this agent can lead to progressive mental confusion, irregular myoclonic jerks, a distinctive pattern of disordered gait, and a variable degree of dysarthria which was fatal to subjects who continued its use[1]. Contrast agents which interfere with or retard solid/plug formation for a particular embolizing agent are also not desirable. Moreover, the contrast agent should be water insoluble and must be encapsulated into the resulting precipitate otherwise adverse medical problems can arise. Complications arising from the use of a water insoluble contrast agents which are not encapsulated into the formed precipitate include particles of contrast agent migrating through the circulation system causing embolization of unintended blood vessels. Complications arising from the use of water soluble contrast agents include dissolution of these agents into the blood upon injection into the vascular site leading to potential systemic side effects in the treated subject. Additionally, the use of water soluble contrast agents limits the clinician's ability to continuously monitor the injection of the embolizing agent into the blood vessel because, upon contact with the blood, the contrast agent is dissolved and removed from the site of injection. As still a further complication, the contrast agent selected must not alter the physical properties of the solution, e.g., viscosity, in such a manner as to render the composition unsuitable for vascular use.

In view of the above, whether an embolizing agent and contrast agent will be suitable in combination to embolize a blood vessel is very empirical and substitution of one embolizing agent for another or one contrast agent with another often leads to deleterious results. This problem is not particularly surprising because ultimately a successful combination of embolizing agent and contrast agent requires compatibility between these components in producing the requisite coherent precipitate having the contrast agent encapsulated therein as well as maintaining the requisite properties for vascular use. When, for example, one contrast agent is replaced by another contrast agent, the chemical and physical properties of each contrast agent will dictate whether it is compatible with the selected embolizing agent.

Accordingly, it is not unexpected that contrast agents having different chemical and/or physical properties will result in changes in the overall properties of the embolizing composition.

This invention is directed to our discovery of a novel injectable liquid embolizing composition comprising an ethylene vinyl alcohol copolymer dissolved in a biocompatible solvent and a water insoluble contrast agent selected from either tantalum, tantalum oxide, or barium sulfate. Surprisingly, this embolizing composition is easily delivered to the vascular site and rapidly forms a coherent solid material which readily encapsulates the contrast agent.

Heretofore, Taki, et al.[2] disclose an example of an embolizing composition containing an ethylene vinyl alcohol copolymer (67 mole percent ethylene and 33 mole percent vinyl alcohol) and a water soluble contrast agent (metrizamide) in DMSO. An apparently similar composition was also disclosed by Terada, et al.[3] However, the water soluble contrast agents disclosed in these references significantly limit the suitability of these compositions for use in embolizing blood vessels. Moreover, as above, the apriori substitution of a water insoluble contrast agents for metrizamide is inherently problematic because it is unpredictable what affect the different chemical and/or physical properties of the water insoluble contrast agent as compared to the soluble contrast agent will have on the ultimate properties of the resulting compositions.

SUMMARY OF THE INVENTION

As above, this invention is directed to our discovery of a novel injectable liquid embolizing composition comprising an ethylene vinyl alcohol copolymer dissolved in dimethylsulfoxide or other suitable biocompatible solvent and a water insoluble contrast agent selected from tantalum, tantalum oxide, or barium sulfate.

Accordingly, in one of its composition aspects, this invention is directed to a composition composition comprising:

(a) from about 2.5 to about 8 weight percent of an ethylene vinyl alcohol copolymer embolizing agent;

(b) from about 10 to about 40 weight percent of a water insoluble contrast agent selected from the group consisting of tantalum, tantalum oxide and barium sulfate;

(c) from about 52 to about 87.5 weight percent of a biocompatible solvent wherein the weight percent of each of the components is based on the total weight of the complete composition.

In one of its method aspects, this invention is directed to a method for embolizing a blood vessel by injecting into said blood vessel a sufficient amount of an embolizing composition comprising:

(a) from about 2.5 to about 8 weight percent of an ethylene vinyl alcohol copolymer embolizing agent;

(b) from about 10 to about 40 weight percent of a water insoluble contrast agent selected from the group consisting of tantalum, tantalum oxide and barium sulfate;

(c) from about 52 to about 87.5 weight percent of a biocompatible solvent wherein the weight percent of each of the components is based on the total weight of the complete composition under conditions wherein a precipitate is formed which embolizes the blood vessel.

In a preferred embodiment, the molecular weight of the ethylene vinyl alcohol copolymer composition is selected such that a solution of 6 weight percent of the ethylene vinyl alcohol composition, 35 weight percent of a tantalum contrast agent in DMSO has a viscosity equal to or less than 60 centipoise at 20° C. and more preferably 40 centipoise or less at 20° C. In another preferred embodiment, the ethylene vinyl alcohol copolymer composition comprises from about 25 to about 60 mole percent of ethylene and from about 40 to about 75 mole percent of vinyl alcohol.

Preferably, the biocompatible solvent is dimethylsulfoxide.

DETAILED DESCRIPTION OF THE INVENTION

This invention is directed to specific embolizing compositions comprising a specific embolizing agent, specific contrast agents and a biocompatible solvent.

Prior to discussing this invention in further detail, the following terms will first be defined:

The term "embolizing" as used in conjunction with "embolizing compositions" and "embolizing agents" refers to a process wherein a material is injected into a blood vessel which thereafter fills or plugs the blood vessel and/or encourages clot formation so that blood flow through the vessel ceases. The embolization of the blood vessel is important in preventing/controlling bleeding (e.g., organ bleeding, gastrointestinal bleeding, vascular bleeding, bleeding associated with an aneurysm) or to ablate diseased tissue (e.g., tumors, etc.) by cutting off its blood supply.

The term "ethylene vinyl alcohol copolymers" refers to copolymers comprising residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers used herein are either commercially available or can be prepared by art recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/ hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels.

The term "contrast agent" refers to a radiopaque material capable of being monitored during injection into a mammalian subject by, for example, radiography. The term "water insoluble contrast agent" refers to contrast agents which are essentially insoluble in water (i.e., having a water solubility of less than 0.01 mg/ml at 20° C.). The water insoluble contrast agents included within the scope of this invention are tantalum, tantalum oxide and barium sulfate, each of which is commercially available in the proper form for in vivo use including a particle size of about 10 μm or less. Other contrast agents suitable for use herein include gold and platinum.

The term "biocompatible solvent" refers to an organic material liquid at least at body temperature of the mammal in which the ethylene vinyl alcohol copolymer is soluble and, in the amounts used, is substantially non-toxic. Suitable biocompatible solvents include, by way of example, dimethylsulfoxide, analogues/homologues of dimethylsulfoxide, and the like. Preferably, the biocompatible solvent is dimethylsulfoxide.

The term "encapsulation" as used relative to the contrast agent being encapsulated in the precipitate is not meant to infer any physical entrapment of the contrast agent within the precipitate much as a capsule encapsulates a medicament. Rather, this term is used to mean that the contrast agent and copolymer form an integral coherent precipitate which does not separate into a copolymer component and a contrast agent component.

Compositions

The compositions of this invention are prepared by conventional methods whereby each of the components is added and the resulting composition mixed together until the overall composition is substantially homogeneous. Specifically, sufficient amounts of the ethylene vinyl alcohol copolymer are added to the biocompatible solvent to achieve the effective concentration for the complete embolizing composition. Preferably, the embolizing composition will comprise from about 2.5 to about 8 weight percent of the ethylene vinyl alcohol copolymer composition based on the total weight of the embolizing composition and more preferably from about 4 to about 5.2 weight percent. If necessary, gentle heating and stirring can be used to effect dissolution of the copolymer into the biocompatible solvent, e.g., 12 hours at 50° C.

Sufficient amounts of the contrast agent are then added to the biocompatible solvent to achieve the effective concentration for the complete embolizing composition. Preferably, the embolizing composition will comprise from about 10 to about 40 weight percent of the contrast agent and more preferably from about 20 to about 40 weight percent and even more preferably 35 weight percent. Insofar as the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Methods

The compositions described above are then employed in methods for embolizing mammalian blood vessels.

Specifically, a sufficient amount of this composition is introduced into the selected blood vessel by conventional means (e.g., injection or catheter delivery under fluoroscopy) so that upon precipitation of the ethylene vinyl alcohol copolymer, the blood vessel is embolized. The particular amount of embolizing composition employed is dictated by the total volume of the vasculature to be embolized, the concentration of copolymer in the composition, the rate of precipitation (solids formation) of the copolymer, etc. Such factors are well within the skill of the art. The rate of precipitation can be controlled by changing the overall hydrophobicity/hydrophilicity of the copolymer with faster precipitation rates being achieved by a more hydrophobic copolymer composition which, in turn, can be achieved by increasing the ethylene content of the copolymer composition.

One particularly preferred method for delivering the embolizing compositions of this invention to the selected vascular site is via a small diameter medical catheter. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

When delivered by catheter, the injection rate dictates, in part, the form of the precipitate at the vascular site. Specifically, low injection rates of approximately 0.05 to 0.3 cc/minute will provide for a precipitate in the form of a kernel or nodule which is particularly beneficial for site specific embolization because the precipitate forms primarily at the point of injection. Contrarily, high injection rates of about 0.1 to 0.5 or more cc/several seconds (e.g., up to ten seconds) will provide for a filament like mass projecting down stream from the catheter tip which is particularly beneficial for providing the embolizing agent deep into the vascular tree. Such procedures are suitable for embolizing tumor masses, organs and arteriovenous malformations (AVM).

When introduced into the vascular site, the biocompatible solvent diffuses rapidly into the blood and a solid precipitate forms which precipitate is the ethylene vinyl alcohol copolymer with the contrast agent encapsulated therein. Without being limited to any theory, it is believed that initially, a soft gel to spongy solid precipitate forms upon contact with the blood which precipitate is open and fibrous in structure. This precipitate then restricts blood flow, entrapping red cells thereby causing clot embolization of the blood vessel.

Utility

The compositions described herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.). Accordingly, these compositions find use in human and other mammalian subjects requiring embolization of blood vessels.

Additionally, these compositions provide an appropriate vehicle for the delivery of a medicament to the vascular site.

7

Specifically, a suitable medicament, e.g., a chemotherapeutic agent, growth factor agents, anti-inflammatory agents, anti-spasmatic agents, etc. which are compatible with the embolizing composition can be included in this composition in therapeutic levels and delivered directly to the vascular site.

The following examples are set forth to illustrate the claimed invention and are not to be construed as a limitation thereof.

EXAMPLES

Unless otherwise stated, all temperatures are in degrees Celsius. Also, in these examples, unless otherwise defined below, the abbreviations employed have their generally accepted meaning:

cc=cubic centimeter

DMSO=dimethylsulfoxide

EVOH=ethylene vinyl alcohol copolymer gm=gram mL=milliliters mm=millimeter psi=pounds per square inch Example 1

The purpose of this example is to demonstrate the suitability of ethylene vinyl alcohol copolymer compositions in DMSO as embolizing agents. The tests were conducted by addition of the copolymer solution into saline and determining the precipitation parameters. Rapid formation of a coherent precipitation evidences suitability of the copolymer composition as an embolizing agent.

Specifically, five ethylene vinyl alcohol copolymer resins were employed of varying concentrations—27, 32, 38, 44 and 48 mole percent ethylene (available from EVAL Company of America, Lisle, Ill., USA) having a viscosity grade as defined by a melt index of about 4–15 (gm/10 minutes) at 210° C. The resin appears as clean, translucent cylindrical particles about 1×2 mm. Samples were prepared at 5.2% concentration in DMSO (obtained from Aldrich Chemical Company, Milwaukee, Wis., USA as M8180-2, 99+% purity). Dissolution was complete within 24 hours at 52° C.

Approximately 0.1 to 0.5 mL of each solution was added by needle/syringe to a normal saline solution at 37° C. or at room temperature. All five samples immediately generated a white mass or string of polymer upon contact with saline. As the ethylene content in the sample increased, the resulting precipitate was whiter, tougher and more dense. The two lowest ethylene content resins appeared to yield a weaker, more gelatinous mass, which nevertheless were suitable for use as embolizing agents.

Accordingly, these results indicate that EVOH copolymers are suitable embolizing agents.

Flow rates were assessed for each of these samples at 10 psi and 37° C. over 3 minutes using a 3 French Infusion catheter (available from Micro Therapeutics, Inc., Aliso Viejo, Calif., USA) in order to assess suitability for catheter delivery of these compositions to the vascular site. The results of this analysis are set forth in Table I below:

8

TABLE I

| Ethylene Content in EVOH Copolymer | Flow Rate |
|---|---|
| 27% | 0.22 cc/min |
| 32% | 0.25 cc/min |
| 38% | 0.20 cc/min |
| 44% | 0.25 cc/min |
| 48% | 0.30 cc/min |

The above results indicate that these compositions possess flow rates suitable for catheter delivery to the vascular site. These results also suggest that preferable results are achieved using a more hydrophobic EVOH composition (e.g., about 48 mole % ethylene content) at a concentration of about 2.5 to about 8.0 weight percent.

Example 2

The purpose of this example is to illustrate that not all polymers are suitable as embolizing agents. Specifically, in this example, the EVOH copolymers described above were replaced with polyurethane (DOW PELLETHANE 2363-80A, Dow Chemical Company, Midland, Mich., USA), polymethylmethacrylate (available from Rohm & Haas, Philadelphia, Pa., USA), polycarbonate (MOBAY MAKROLON 2558-1112, Mobay Chemical Company, Bayer Inc., Pittsburgh, Pa., USA), two different cellulose diacetates [Cellulose Acetate NF CA 320-S (~32% acetyl content) and Cellulose Acetate NF CA 398-10 (~39.8 acetyl content) both available from FMC Corp., Pharmaceutical Division, Philadelphia, Pa., USA)] and cellulose triacetate (Cellulose Acetate NF CA 435-75S (~43.5% acetyl content)—FMC Corp., Pharmaceutical Division, Philadelphia, Pa., USA).

The results of this analysis indicated that polyurethane samples were slow to dissolve in DMSO at 52° C. and, upon cooling to room temperature, formed a high viscosity solution/gel unsuitable for injection. In the case of the polymethylmethacrylate, the polymer dissolved in DMSO but the precipitate formed upon addition to saline was unsuitable for use as an embolizing agent because it lacked cohesiveness and easily fragmented. In the case of the polycarbonate, the polymer failed to dissolve in DMSO at 52° C. over 3 days. The cellulose triacetate sample provided too high a viscosity for effective delivery via a catheter at a concentration sufficient to effectively embolize a blood vessel and reduction of the concentration to less than 2.5 weight percent resulted in precipitate formation which was unsuitable for vascular embolization. Only the cellulose diacetates provided suitability for vascular embolization in a manner similar to EVOH and the use of such polymers as embolizing agents is described in further detail in U.S. patent application Ser. No. 08/508,248 filed concurrently herewith as Attorney Docket No. 018413-003 entitled "CELLULOSE DIACETATE COMPOSITIONS FOR USE IN EMBOLIZING BLOOD VESSELS" which application is incorporated herein by reference in its entirety.

Example 3

The purpose of this example is to compare in vitro results achieved by incorporating a water soluble contrast agent and a water insoluble contrast agent of this invention into an embolizing composition containing EVOH in DMSO. Specifically, in this example, an EVOH composition (44 mole percent ethylene) was dissolved into DMSO to provide for an 6.8 weight percent concentration of the copolymer in DMSO. To this solution was added either tantalum (10 weight percent, available from Leico Industries, New York, N.Y., USA, 99.95% purity, less than 43 µm in size) as a water insoluble contrast agent or metrizamide (38.5 weight percent, available from Aldrich Chemical Company, Milwaukee, Wis., USA) as a water soluble contrast agent. Because these results are in vitro results, the tantalum particle size is not important and the larger particles size is not expected to affect these results.

In the tantalum composition, tantalum settling can result from prolonged standing. Sonification may help but thorough mixing prior to use is required.

Approximately 0.2 mL of the each composition was then added by syringe/needle to a saline solution at 37° C. and the characteristics of the resulting precipitate examined. In the case of the tantalum sample, a precipitate immediately formed which was characterized by firm spongy filaments and nodules. The metrizamide sample on the other hand did not form a well defined solid mass as the metrizamide rapidly diffused away.

Example 4

The purpose of this example is to illustrate that certain embolizing agent/contrast agent combinations provide for physical properties which makes injection of the combination into vascular sites significantly more difficult. Specifically, in this example, a composition comprising 6.8 weight percent of EVOH (44 mole percent ethylene) in DMSO was prepared. The viscosity of this composition was approximately 60 centipoise at 20° C. Upon addition of 38.5 weight percent of metrizamide to this composition, the viscosity increased significantly to approximately 145 centipoise at 20° C.

Contrarily, the addition of 35 weight percent of tantalum or barium sulfate to a similar EVOH/DMSO composition did not materially alter the viscosity of the composition.

The above results indicate that the use of tantalum as the contrast agent provides for compositions with significantly lower viscosity than those employing metrizamide. In turn, such lower viscosities render the compositions easier to deliver either by injection or by catheter to the vascular site thereby proportionally reducing the likelihood of vascular injury.

Example 5

The purpose of this example is to illustrate an in vivo application of the embolizing composition of this invention.

In this example, a 50 pound male hound was prepared for blood vessel embolization using an embolic composition comprising 5.8 weight percent EVOH polymer (containing 48 weight percent ethylene), 20 weight percent tantalum in DMSO was loaded into a syringe. Embolization of the left kidney proceeded by placement of a 3F micro catheter into the kidney through a 5F AngioDynamics Headhunter catheter. The catheter was advanced into the renal artery, flushed with contrast agent to identify the location and then flushed with DMSO, followed by 0.3 cc of the EVOH composition described above, followed yet by more DMSO within the catheter. The EVOH composition was quickly injected into the renal artery. After delivery of about 0.2 cc of EVOH composition, the upper pole of the kidney was blocked. Delivery of the remaining EVOH composition resulted in the entire kidney being embolized.

The above results indicate that the compositions of this invention are suitable for in vivo embolization of blood vessels in mammalian subjects.

From the foregoing description, various modifications and changes in the composition and method will occur to those skilled in the art. All such modifications coming within the scope of the appended claims are intended to be included therein.

What is claimed is:

1. A composition comprising:
   (a) from about 2.5 to about 8.0 weight percent of an ethylene vinyl alcohol copolymer;
   (b) from about 10 to about 40 weight percent of a water insoluble contrast agent selected from the group consisting of tantalum, tantalum oxide and barium sulfate;
   (c) from about 52 to about 87.5 weight percent of a biocompatible solvent
   wherein the weight percent of each of the components is based on the total weight of the complete composition.

2. The composition according to claim 1 wherein said ethylene vinyl alcohol copolymer comprises from about 25 to about 60 mole percent of ethylene and from about 40 to about 75 mole percent of vinyl alcohol.

3. The composition according to claim 2 wherein said biocompatible solvent is DMSO.

4. The composition according to claim 3 wherein said contrast agent is tantalum.

5. The composition according to claim 3 wherein said contrast agent is tantalum oxide.

6. The composition according to claim 3 wherein said contrast agent is barium sulfate.

7. A method for embolizing a blood vessel by injecting into said blood vessel a sufficient amount of an embolizing composition comprising:
   (a) from about 2.5 to about 8.0 weight percent of an ethylene vinyl alcohol copolymer embolizing agent;
   (b) from about 10 to about 40 weight percent of a water insoluble contrast agent selected from the group consisting of tantalum, tantalum oxide and barium sulfate;
   (c) from about 52 to about 87.5 weight percent of a biocompatible solvent
   wherein the weight percent of each of the components is based on the total weight of the complete composition under conditions wherein a precipitate is formed which embolizes the blood vessel.

8. The method according to claim 7 wherein said ethylene vinyl alcohol copolymer comprises from about 25 to about 60 mole percent of ethylene and from about 40 to about 75 mole percent of vinyl alcohol.

9. The method according to claim 8 wherein said biocompatible solvent is DMSO.

10. The method according to claim 9 wherein said contrast agent is tantalum.

11. The method according to claim 9 wherein said contrast agent is tantalum oxide.

12. The method according to claim 9 wherein said contrast agent is barium sulfate.

13. The method according to claim 7 wherein the embolizing composition is injected into the blood vessel at a rate of about 0.05 to 0.3 cc/minute.

14. The method according to claim 7 wherein the embolizing composition is injected into the blood vessel at a rate of at least 0.6 cc/minute.

15. The method according to claim 14 wherein the injection rate of at least 0.6 cc/minute is employed to form a filament like mass projecting down stream from the catheter tip for embolizing tumor masses, organs and arteriovenous malformations (AVM).

* * * * *